United States Patent [19]

Erwin

[11] 4,083,864

[45] Apr. 11, 1978

[54] METHOD FOR THE PRODUCTION OF N-ALKYL BETA-HYDROXYLAMINE HYDROCINNAMONYL HYDROXAMIC ACIDS

[75] Inventor: Robert Erwin, Buffalo, N.Y.

[73] Assignee: Research Corporation, New York, N.Y.

[21] Appl. No.: 691,788

[22] Filed: Jun. 1, 1976

[51] Int. Cl.² .............................................. C07C 83/10
[52] U.S. Cl. ..................... 260/500.5 H; 260/340.9 R; 260/307 B; 424/315
[58] Field of Search ................................ 260/500.5 H

[56] References Cited

U.S. PATENT DOCUMENTS

| 2,279,560 | 4/1942 | Dietrich | 260/500.5 H |
| 3,474,132 | 10/1969 | Bernstein | 260/500.5 H |

Primary Examiner—Joseph E. Evans
Attorney, Agent, or Firm—Holman & Stern

[57] ABSTRACT

The subject invention is directed to a method of making compounds having the formula:

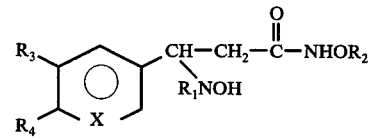

wherein $R_1$ is alkyl, $R_2$ is H or alkyl, $R_3$ and $R_4$ are H, halogen, amino, alkylamino, alkoxy, alkyl, OH, O, $NO_2$ or combinations thereof, and X is CH or N, which compounds are useful as antihypertensive agents.

9 Claims, No Drawings

METHOD FOR THE PRODUCTION OF N-ALKYL BETA-HYDROXYLAMINE HYDROCINNAMONYL HYDROXAMIC ACIDS

BACKGROUND OF THE INVENTION

The subject invention is directed to hydrocinnamonylhydroxamic acid derivatives which are useful as anti-hypertensive agents.

There are a number of agents presently known which have been used in the treatment of hypertensive crisis. Such agents are utilized to bring about a drop in blood pressure until subsequent measures can be taken to maintain and stabilize a patient suffering with hypertension. Those agents presently available for treatment have been found to act by one of three methods. That is to say that said agents act by suppressing the sympathetic nervous system, by directly relaxing vascular smooth muscle, or by contracting extracellular and plasma volumes with a temporary reduction in cardiac output. In the presence of hypertensive crisis, however, only parenterally administered agents that act directly on vascular smooth muscle have been found to be of particular utility. In this connection it is noted that the ideal dilating agent should reduce peripheral vascular resistance without affecting the heart and/or the sympathetic nervous system. Thus, its hemodynamic action should promote adequate tissue perfusion without compromising cardiovascular reflex regulatory mechanisms.

Hydroxamic acid derivatives have previously been disclosed to have utility as pharmaceutical agents in the treatment of various diseases. In particular hydrocinnamonylhydroxamic acid derivatives have been disclosed to have anti-hypertensive actions when administered to warm blooded animals. The subject invention is distinguished from said previously disclosed derivatives both in terms of structure and in the substantially improved results obtained from the use thereof.

DETAILED DESCRIPTION OF THE INVENTION

The object of the subject invention is to produce a new method for making hydrocinnamonylhydroxamic acid derivatives which are useful as anti-hypertensive agents.

In particular the subject invention is directed to compounds having the general formula:

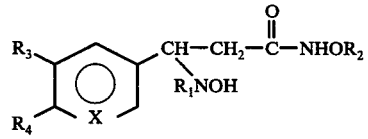

I wherein $R_1$ represents alkyl, $R_2$ represent hydrogen or alkyl, $R_3$ and $R_4$ represent hydrogen, halogen, such as chloro, fluoro, iodo and/or bromo, amino, alkylamino, alkoxy, alkyl, hydroxyl, oxygen, $NO_2$, phenyl, NHOH, or combinations thereof, and X is CH or N and pharmaceutically tolerable salts thereof, which are biologically active in reducing an elevated blood pressure in warm blooded animals.

The novel compounds of the subject invention having the structure:

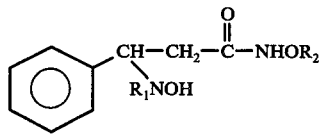

II wherein $R_1$ represents alkyl and $R_2$ represents hydrogen or alkyl, are prepared from a novel process. According to the state of the art, it had been thought that one could prepare the above-noted compound (II) simply by adding N-methyl-hydroxylamine across the C=C bond of cinnamic acid ethyl ester and simultaneously cleaving the ester linkage with N-methyl-hydroxylamine. It was found however that instead of the desired novel compound, the di-N-methyl analog, an isoxazolone was obtained. Therefore the preparation of the subject novel compound by a mere extension of the known process proved to be impossible.

In a co-pending application filed on even date herewith in the name of Kenneth R. Fountain, Horst Kehl and Terry Early and entitled "Anti-Hypertensive Compounds" the compounds noted above are claimed.

As previously noted the novel compounds of the subject invention have been found to be pharmacologically active as anti-hypertensive agents. That is to say said compounds act as potent vasodepressor agents in warm blooded animals having an elevated or normal blood pressure. Moreover, said compounds act in the presence of a histamine block, a cholinergic block, and both α and β-adrenergic blocks and are, therefore, considered directly acting.

In the specification the term "halogen" includes fluorine, chlorine, bromine and iodine. The preferred alkyl and alkoxy groups contain from 1 to 7 carbon atoms.

The subject invention will be illustrated by the following more detailed Examples thereof, in which Example I illustrates the prior art method by which the ring substituted compounds are made, while Example II illustrates the novel method of the present invention for making the N-substituted compounds.

EXAMPLE I (3-(m-chloro-phenyl-3-hydroxyaminopropionhydroxamic acid)

A solution of 6.55 g (0.094 mole) of hydroxylamine hydrochloride in 35–50 ml of methanol was made up at the boiling point of the methanol. This mixture was cooled at room temperature and 20.35 g of a 25% solution of sodium methoxide in methanol was added (0.0942 mole). The resulting suspension was thoroughly chilled in an ice-water bath and the pH was adjusted to approximately 8 with hydrion paper, as an indicator, and either hydroxylamine hydrochloride or sodium methoxide as required. The white salt was filtered and the clear hydroxyl amine solution was added to 5.73 g (0.0314 mole) cinnamate ester in methanol and the volume adjusted to 100 ml by addition of methanol. This mixture was allowed to stand at 25° for 3 hours then stored for 48 hours at 5° in a refrigerator. At the end of this period a white solid was formed. Filtration gave 4.701 g (or 65% of theory) m.p. 126°–126.5° C. Concentration of the mother liquor gave a white powder which when recrystallized from methanol gave 1.05 g of further pure compound bringing the total to 5.751 g (or 79%). Anal. calc'd. for $C_9H_{14}N_3O_4Cl$ (the hydroxylamine salt of 3-(m-chloro-phenyl)-3-hydroxyaminopropionhydroxamic acid): C, 41.00; H, 5.35; N, 15.94. Found: C, 41.05; H, 5.36; N, 15.73. The spectral data for this compound are: IR(nujol) $\mu$OH 3210 cm$^{-1}$ NH 3080-2750 cm$^{-1}$ broad; $\nu$C=O 1658 cm$^{-1}$; NH 1620 cm$^{-1}$; and bands at 788 cm$^{-1}$ and 700 cm$^{-1}$ characteristic of phenyl ring.

EXAMPLE II

A saturated solution of N-methylhydroxylamine hydrochloride in methanol was made by dissolving 16.2 g (0.2 mole) of N-methylhydroxylamine hydrochloride in the minimum amount of methanol at the boiling point. Similarly a solution of 11.2 g (0.2 mole) of potassium hydroxide was made up. These solutions were mixed at room temperature and the resulting thick white slurry cooled at 0° in an ice-water bath. Filtration then gave a clear N-methylhydroxylamine solution to which 7.6 g (0.1 mole) of ethyl cinnamate were added. The reaction mixture was allowed to stand for 30 hours and the solvent was removed on a rotary evaporator. The remaining material was taken up into 45 ml of diethyl ether which left a gummy mass at the bottom of the flask. After filtration a thick oil separated out, which was removed by means of a pipette. Removal of the ether after this operation gave the isoxazolone

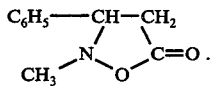

To this isoxazolone was added a solution of hydroxylamine made by preparing a saturated solution of 13.9 g (0.2 mole) of hydroxylamine hydrochloride and a solution of 11.2 g (0.2 mole) of potassium hydroxide in methanol as above. After five minutes of standing the bottom of the flask was scratched and there was deposited 16.54 (79%) of the product (m.p. 116°–117° C). A further crop of crystals, 3.44 g, brought the yield to 19.98 g or 95.3% of theory from the ester. Spectral properties were: IR(nujol) OH at 3210 cm$^{-1}$; C=O at 1640 cm$^{-1}$ NMR($d_6$-acetone-H$_2$O = 2.55 (singlet, 3H); 2.95 (doublet, 2H); 4.15 (multiplet, 1H); 7.45 (singlet, 5H).

The isoxazolone (1) had C=O at 1790 and 1775 cm$^{-1}$ (doublet); no OH NMR was (in CDCl$_3$) 2.73 (singlet, 3H); 2.95 (doublet, 2H); 4.15 (multiplet, 1H); 7.45 (singlet, 5H). A hydrazide of the isoxazolone was made to complete its structure proof. Anal. calc'd. for C$_{10}$H$_{15}$N$_3$O$_2$: C, 57.40; H, 7.23; N, 20.08. Found: C, 57.18; H, H7.27; N, 20.08.

EXAMPLES III–VIII

The following compounds having the following analyses were prepared according to the appropriate method of either Example I (the m-halo derivatives) or Example II (the N-alkyl derivatives)

| Example | Formula (m.p.) | Theoretical | | | Analysis Actual | | |
|---|---|---|---|---|---|---|---|
| | | C | H | N | C | H | N |
| III | m-FC$_9$H$_{14}$N$_3$O$_4$ (125–126.5%) | 43.72 | 5.71 | 17.00 | 43.7 | 5.73 | 16.94 |
| IV | m-BrC$_9$H$_{14}$N$_3$O$_4$O . 5H$_2$O (117–118°) | 34.08 | 4.77 | 13.25 | 34.28 | 4.21 | 12.73 |
| V | C$_8$H$_{12}$N$_3$O$_2$Cl (m-chloro) (123–125%) (decomposed) | 41.02 | 5.17 | 17.97 | 40.57 | 4.75 | 17.92 |
| VI | C$_{10}$H$_{14}$N$_2$O$_3$ (N-methyl) (118–120°) | 57.13 | 6.71 | 13.32 | 57.16 | 6.53 | 13.41 |
| VII | C$_{11}$H$_{16}$N$_2$O$_3$ . 5H$_2$O (N-ethyl) (98–103°) (decomposed) | 56.64 | 7.35 | 12.00 | 56.07 | 6.98 | 11.96 |
| VIII | C$_{16}$H$_{26}$N$_2$O$_3$ . 5H$_2$O (N-heptyl) (79–81°) | 63.2 | 8.90 | 9.23 | 62.21 | 8.87 | 10.01 |

EXAMPLE IX

Mongrel dogs of both sexes weighing from 15.0–22.0 kg were anesthetized with pentobarbital (30 mg/kg iv). A femoral artery was cannulated and the systemic blood pressure was recorded with a Statham pressure transducer and a Grass model 5 polygraph. Quantitative evaluation of blood pressure achieved by internal calibration of the polygraph checked against direct manometric readings. Respiration was recorded with a conventional pneumograph.

For the studies in the conscious co-operative subject, the animal (dog) was surgically modified to provide direct access to either the femoral or carotid artery by implantation of a polyvinyl catheter filled with heparin solution (1 mg/ml). After surgical recovery and adequate healing had occurred the animal was trained to stand on the table so that blood pressure could be recorded during the experiment. An ordinary intravenus (iv) set-up provided access to a vein during the experiment for repeated injections of experimental compounds as well as other drugs. When experimental compounds were given as a continuous infusion the iv set-up was replaced with a peristaltic pump and the infusion rate was measured with the aid of a "Manostat" flowmeter. All of the novel derivatives were prepared in such a manner to be injected in either saline or a buffer solution to be biologically compatible.

The blood pressure changes observed at varying dose levels of each of several different injected derivatives, are set forth in Table I, below:

TABLE I

| Compounds Structure and Name | | 10⁻² | 5×10⁻² | 10⁻¹ | 2×10⁻¹ | 2×10⁻¹ | 5×10⁻¹ | Dose, mg/kg 1.0 | 1.5 | 2.0 | 3.0 | 5.0 | 10.0 | 20.0 | mm Hg R |
|---|---|---|---|---|---|---|---|---|---|---|---|---|---|---|---|
| 1. Structure with Me, OH, N, CH-CH₂-phenyl, O=C-N-OH | N—Me—HCHA | 13±3 / 15±0 | 15±0 / 15±0 | 17±3 / 17±3 | 29±7 / 37±8 | | 44±8 / 50±9 | 63±8 / 64±3 | | 75±10 / 70±9 | | 80±7 / 72±8 | 81±3 / 72±5 | | Systolic / Diastolic |
| 2. Structure with Et | N—Et—HCHA | | | NC | 5±5 / 5±5 | 5±2 / 9±4 | 10±3 / 20±2 | 46±12 / 39±10 | | 69±7 / 62±9 | | 89±3 / 77±2 | 90±5 / 78±9 | 90±2 / 78±4 | Systolic / Diastolic |
| 3. Structure with 1-hept | N—hept—HCHA | | | | | NC | 7±7 / 6±7 | 20±7 / 30±8 | | | 60±5 / 60±4 | | | | Systolic / Diastolic |
| 4. Structure with Cl | m-Cl—HCHA | 12±5 / 9±3 | 33±7 / 34±7 | 50±0 / 45±5 | 60±4 / 55±7 | 73±5 / 63±1 | 85±7 / 74±5 | 100±10 / 80±6 | | 104±7 / 85±5 | 108±4 / 85±5 | 110±3 / 85±2 | 109±4 / 87±7 | | Systolic / Diastolic |
| 5. Structure with Br | m-Br—HCHA | 5±0 / 5±0 | 22±3 / 23±0 | 31±0 / 30±8 | 40±5 / 44±7 | | 45±10 / 51±11 | 54±12 / 58±8 | 56±4 / 45±9 | 59±5 / 50±5 | 60±5 / 67±3 | 62±3 / 63±5 | 61±4 / 68±7 | | Systolic / Diastolic |
| 6. Structure with methylenedioxy—OCH₃ | | NC | 22±3 / 17±6 | 18±4 / 23±3 | 35±6 / 47±4 | | 35±0 / 55±5 | 47±3 / 62±2 | | 55±5 / 65±6 | | 55±7 / 65±5 | | | Systolic / Diastolic |

EXAMPLE X

The following derivatives were tested to determine their activity in the presence of a histamine blocking agent; atropine; beta adrenergic blocking agent; and an alpha adrenergic blocking agent. By administering said derivatives in the presence of each of the above noted agents with the following results:

TABLE II

| Compound | Dose | Control | Diphenhydramine (2.0mg/kg) | Atropine (0.5mg/kg) | beta-block' | Alpha-block" | mm Hg Reduction |
|---|---|---|---|---|---|---|---|
| N—Et—HCHA | 0.5mg/kg | 10 ≠ 3 | 11 ≠ 5 | 12 ≠ 5 | 10 ≠ 7 | 10 ≠ 9 | Systolic |
|  |  | 20 ≠ 2 | 18 ≠ 7 | 19 ≠ 8 | 14 ≠ 7 | 13 ≠ 10 | Diastolic |
|  | 1.0mg/kg | 46 ≠ 12 | 43 ≠ 9 | 48 ≠ 11 | 40 ≠ 10 | 38 ≠ | Systolic |
|  |  | 38 ≠ 10 | 41 ≠ 9 | 37 ≠ 8 | 34 ≠ 10 | 32 ≠ 9 | Diastolic |
| N—Me—HCHA | 0.1mg/kg | 17 ≠ 3 | 20 ≠ 10 | 17 ≠ 9 | 14 ≠ 9 | 14 ≠ 9 | Systolic |
|  |  | 17 ≠ 3 | 19 ≠ 5 | 17 ≠ 7 | 12 ≠ 10 | 14 ≠ 8 | Diastolic |
|  | 0.5mg/kg | 44 ≠ 8 | 41 ≠ 10 | 42 ≠ 9 | 38 ≠ 11 | 35 ≠ 12 | Systolic |
|  |  | 50 ≠ 9 | 48 ≠ 8 | 46 ≠ 11 | 39 ≠ 10 | 31 ≠ 11 | Diastolic |
|  | 1.0mg/kg | 63 ≠ 8 | 58 ≠ 12 | 60 ≠ 8 | 54 ≠ 9 | 52 ≠ 10 | Systolic |
|  |  | 64 ≠ 3 | 60 ≠ 11 | 60 ≠ 10 | 50 ≠ 11 | 48 ≠ 12 | Diastolic |
| m-Br—HCHA |  | 31 ≠ 10 | 33 ≠ 9 | 31 ≠ 10 | 31 ≠ 9 | 29 ≠ 11 | Systolic |
|  | 0.1mg/kg | 30 ≠ 8 | 34 ≠ 11 | 33 ≠ 12 | 33 ≠ 10 | 30 ≠ 7 | Diastolic |
|  |  | 45 ≠ 10 | 40 ≠ 9 | 43 ≠ 11 | 40 ≠ 8 | 39 ≠ 12 | Systolic |
|  | 0.5mg/kg | 44 ≠ 7 | 46 ≠ 13 | 42 ≠ 9 | 38 ≠ 11 | 38 ≠ 11 | Diastolic |
|  |  | 54 ≠ 8 | 58 ≠ 12 | 57 ≠ 9 | 51 ≠ 9 | 49 ≠ 13 | Systolic |
|  | 1.0mg/kg | 58 ≠ 8 | 54 ≠ 7 | 54 ≠ 8 | 50 ≠ 11 | 49 ≠ 9 | diastolic |
| m-Cl—HCHA |  | 33 ≠ 7 | 29 ≠ 10 | 35 ≠ 11 | 30 ≠ 10 | 29 ≠ 11 | Systolic |
|  | 0.05mg/kg | 34 ≠ 7 | 32 ≠ 7 | 31 ≠ 12 | 30 ≠ 7 | 28 ≠ 9 | Diastolic |
|  |  | 50 ≠ 0 | 48 ≠ 10 | 51 ≠ 9 | 47 ≠ 9 | 47 ≠ 10 | Systolic |
|  | 0.1mg/kg | 45 ≠ 5 | 48 ≠ 9 | 43 ≠ 11 | 40 ≠ 11 | 39 ≠ 13 | Diastolic |
|  |  | 85 ≠ 7 | 80 ≠ 12 | 79 ≠ 12 | 71 ≠ 12 | 77 ≠ 10 | Systolic |
|  | 0.5mg/kg | 74 ≠ 5 | 74 ≠ 12 | 76 ≠ 9 | 70 ≠ 10 | 70 ≠ 9 | Diastolic |
|  |  | 100 ≠ 10 | 101 ≠ 9 | 97 ≠ 10 | 89 ≠ 10 | 87 ≠ 12 | Systolic |
|  | 1.0mg/kg | 80 ≠ 6 | 84 ≠ 11 | 86 ≠ 9 | 80 ≠ 11 | 79 ≠ 11 | Diastolic |

'beta block was achieved with either dichloroisoproterenol (10.0mg/kg) or propanolol (0.2mg/kg)
"alpha block was achieved with either phenoxybenzamine (12.0mg/kg) or phentolamine (1.0mg/kg)
The experimental compounds were given in bolus form at the various dose levels and the response compared to the control values. No statistical difference could be determined.

It should be noted that in the tests described above, the compounds were administered intravenously. Other suitable modes of administering, however, can also be used. It has been determined that permeability of the compounds through gut is high and transport across rabbit jejunum occurs by active transport against a concentration gradient. Additionally, an experiment has been performed which appeared to indicate that there is oral activity. From the results of this experiment and the absorption in the gut, it may be preliminarily concluded that the compounds may be administered orally, with the choice of a pharmaceutically acceptable carrier being apparent to one skilled in the art.

While methanol was used as the solvent in the Examples, it is to be distinctly understood that ethanol is equally suitable as well as any other reaction-inert solvent in which the reactants are soluble. Since hydroxylamine hydrochloride was used as a reactant, the alcoholic solvents were used. If the base is used, other solvents such as methylene chloride and tetrahydrofuran may be used.

The proportions of reactants are important to the extent that a molar ratio of hydroxylamine to cinnamic acid ester less than about 2:1 could cause unwanted side reactions which could affect yield and purity of the end product. The preferred lower limit is about 3:1. There is no criticality attached to an upper limit, that is, there is no upper limit except as dictated by economics. Temperature is unimportant to the reactions since they proceed at room temperature and crystallization proceeds best under refrigeration. The time needed to obtain crystallization, for practical purposes, cannot be speeded up—the product spontaneously coming out of the solution when sufficient time has elapsed.

It should be noted, also, that for the production of the methoxy compound, it is necessary to include triethanolamine as a catalyst.

It should now be apparent that the objects set forth at the outset have been successfully achieved. Moreover, while there is shown and described present preferred embodiments of the invention, it is to be distinctly understood that the invention is not limited thereto, but may be otherwise variously embodied and practiced within the scope of the following claims.

I claim:

1. A process for preparing N-alkyl beta-hydroxylamine derivatives of hydrocinnamonylhydroxamic acids which comprises contacting an alkyl cinnamate with N-alkyl-hydroxylamine and subsequently adding hydroxylamine thereto, the molar ratio of said hydroxylamine to said alkyl cinnamate being at least about 2:1.

2. The process of claim 1, wherein said N-alkyl-hydroxylamine is N-methyl hydroxylamine.

3. The process of claim 1, wherein the alkyl group of said N-alkyl-hydroxylamine contains from 1 to 7 carbon atoms.

4. The process of claim 1, wherein said N-alkylhydroxylamine is N-ethyl hydroxylamine.

5. The process of claim 1, wherein said N-alkylhydroxylamine is N-heptyl hydroxylamine.

6. The process of claim 1, wherein said alkyl cinnamate is ethyl cinnamate.

7. The process of claim 1, wherein the molar ratio of said hydroxylamine to said alkyl cinnamate is at least about 3:1.

8. The process of claim 1, wherein said hydroxylamine is added as an equimolar solution of hydroxylamine and an alkali hydroxide.

9. The process of claim 8, wherein said alkali hydroxide is potassium hydroxide.

* * * * *